(12) United States Patent
Fukumoto et al.

(10) Patent No.: US 10,638,077 B2
(45) Date of Patent: Apr. 28, 2020

(54) IMAGING DEVICE AND CONTROL METHOD

(71) Applicant: CANON KABUSHIKI KAISHA, Tokyo (JP)

(72) Inventors: Junya Fukumoto, Yokohama (JP); Yuma Kudo, Kawasaki (JP); Takashi Tsuda, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 130 days.

(21) Appl. No.: 15/952,916

(22) Filed: Apr. 13, 2018

(65) Prior Publication Data
US 2018/0302584 A1    Oct. 18, 2018

(30) Foreign Application Priority Data

Apr. 14, 2017 (JP) .................................. 2017-080974
Apr. 13, 2018 (JP) .................................. 2018-077557

(51) Int. Cl.
*H04N 5/376* (2011.01)
*H04N 5/353* (2011.01)
(Continued)

(52) U.S. Cl.
CPC ......... *H04N 5/3765* (2013.01); *H04N 5/2353* (2013.01); *H04N 5/2354* (2013.01);
(Continued)

(58) Field of Classification Search
CPC ........... H04N 5/23203; H04N 5/23232; H04N 5/2353; H04N 5/2354; H04N 5/3532;
(Continued)

(56) References Cited

U.S. PATENT DOCUMENTS 6,278,490 B1 * 8/2001 Fukuda .................. H04N 5/235
                                                            348/362
6,611,289 B1 * 8/2003 Yu .......................... H04N 9/045
                                                            348/265
(Continued)

FOREIGN PATENT DOCUMENTS

JP       2014-147667       8/2014
JP          5942053        6/2016
(Continued)

*Primary Examiner* — Lin Ye
*Assistant Examiner* — Chriss S Yoder, III
(74) *Attorney, Agent, or Firm* — Venable LLP

(57) ABSTRACT

An imaging device according to an embodiment includes an image sensor, and processing circuitry. The image sensor is a rolling-shutter type image sensor that includes a plurality of pixels that are arranged in a matrix and generate an electric signal due to light received and, on a frame-to-frame basis, repeatedly performs a process to sequentially start to conduct exposure on at least every line, starting from the first line of the pixels to the last line, and output the electric signal sequentially from the line for which exposure has been completed. The processing circuitry causes the pixels to receive light during only a period based on the blanking period that corresponds to the period from when the output of the electric signal from the last line is finished until the output of the electric signal from the first line is started. The processing circuitry generates images in accordance with the electric signal.

20 Claims, 7 Drawing Sheets

(51) Int. Cl.
*H04N 5/372* (2011.01)
*H04N 5/232* (2006.01)
*H04N 5/235* (2006.01)
*H04N 5/369* (2011.01)
*A61B 1/04* (2006.01)
*H04N 5/225* (2006.01)

(52) U.S. Cl.
CPC ..... *H04N 5/23203* (2013.01); *H04N 5/23232* (2013.01); *H04N 5/3532* (2013.01); *H04N 5/3537* (2013.01); *H04N 5/3692* (2013.01); *H04N 5/372* (2013.01); *A61B 1/04* (2013.01); *H04N 2005/2255* (2013.01); *H04N 2209/049* (2013.01)

(58) Field of Classification Search
CPC .... H04N 5/3537; H04N 5/3692; H04N 5/372; H04N 5/3765; H04N 2005/2255; H04N 2209/049; A61B 1/04
See application file for complete search history.

(56) References Cited

U.S. PATENT DOCUMENTS

| | | | |
|---|---|---|---|
| 2013/0208149 A1* | 8/2013 | Kamiya | H04N 5/217 348/241 |
| 2014/0194686 A1 | 7/2014 | Murayama | |
| 2015/0022647 A1 | 1/2015 | Takei et al. | |
| 2016/0317003 A1 | 11/2016 | Ogata et al. | |
| 2016/0360948 A1 | 12/2016 | Mizuno et al. | |

FOREIGN PATENT DOCUMENTS

| JP | 6019167 | 11/2016 |
|---|---|---|
| WO | WO 2014/125724 A1 | 8/2014 |

\* cited by examiner

IMAGING DEVICE AND CONTROL METHOD

CROSS-REFERENCE TO RELATED APPLICATIONS

This application is based upon and claims the benefit of priority from Japanese Patent Application No. 2017-080974, filed on Apr. 14, 2017; and Japanese Patent Application No. 2018-077557, filed on Apr. 13, 2018; the entire contents of which are incorporated herein by reference.

FIELD

Embodiments described herein relate generally to an imaging device and a control method.

BACKGROUND

For imaging devices such as endoscope devices, CCD (charge coupled device) image sensors used to predominate; however, in recent years, CMOS (complementary metal oxide semiconductor) image sensors have been dominant because they offer advantages in a reduction in cost, a single power source, low power consumption, and the like. For CMOS image sensors, a rolling shutter type is typically used.

DETAILED DESCRIPTION

An imaging device according to an embodiment includes an image sensor, and processing circuitry. The image sensor is a rolling-shutter type image sensor that includes a plurality of pixels arranged in a matrix to generate electric signals due to light received and, on a frame-to-frame basis, repeatedly performs a process to sequentially start to conduct exposure on at least every line starting from the first line of the pixels to the last line and output the electric signal sequentially from the line for which exposure has been completed. The processing circuitry causes the pixels to receive light during only a period based on the blanking period that corresponds to the period from when the output of the electric signal from the last line is finished until the output of the electric signal from the first line is started. The processing circuitry generates images on the basis of the electric signal.

With reference to drawings, an explanation is given below of an imaging device and a method of controlling the imaging device according to each embodiment. Furthermore, the embodiment are not limited to the details described below. Moreover, the details described in an embodiment or modification are also applied to other embodiments or modifications in principle.

First Embodiment

Figure 1:
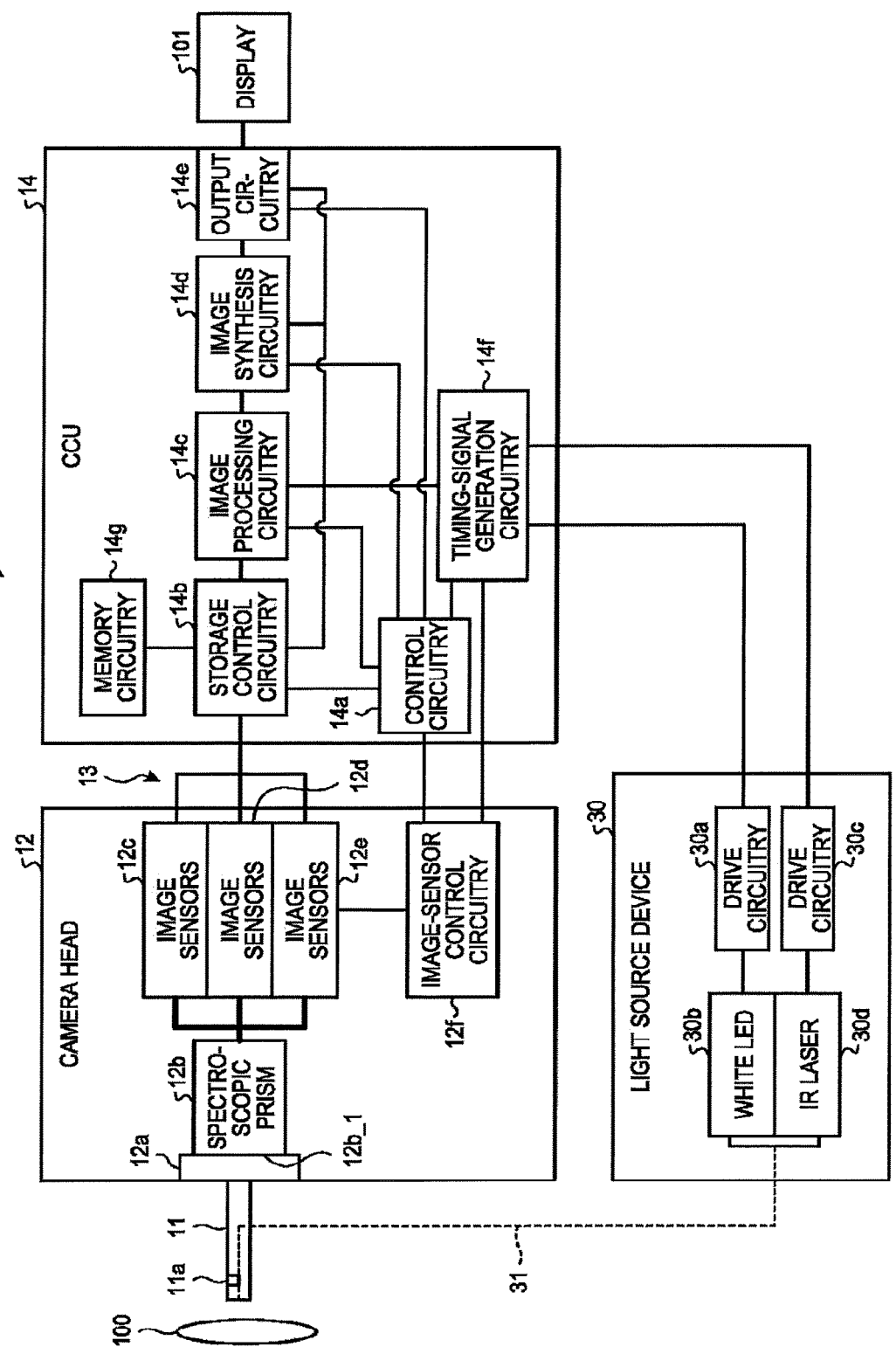
FIG. 1 is a diagram that illustrates an example of the configuration of an imaging system that includes an imaging device according to a first embodiment.

FIG. 1 is a diagram that illustrates an example of the configuration of an imaging system 1 that includes an imaging device 10 according to a first embodiment. As illustrated in FIG. 1, the imaging system 1 according to the first embodiment includes the imaging device 10, a light source device 30, and an optical fiber 31.

For example, the imaging device 10 is a device that is used as a rigid medical endoscope and captures the inside of the body of a subject 100. The imaging device 10 includes a scope 11, a camera head 12, a camera cable 13, and a CCU (camera control unit) 14.

The scope 11 is inserted into the inside of the body of the subject 100 when imaging is conducted. An objective lens 11a is provided at the distal end of the scope 11. The scope 11 is rigid so that it is not bent.

The camera head 12 includes an excitation-light cut filter 12a, a spectroscopic prism 12b, three image sensors 12c to 12e (12c, 12d, 12e), and image-sensor control circuitry 12f.

The excitation-light cut filter 12a is an optical device that is provided by being opposed to imaging areas of pixels and that causes the pixels to receive light other than the excitation light output from the light source device 30. The excitation-light cut filter 12a is a filter that is provided between the scope 11 and an incidence plane 12b_1 of the spectroscopic prism 12b and that cuts excitation light from the light that enters from the objective lens 11a and passes light other than the excitation light. Therefore, the incidence plane 12b_1 of the spectroscopic prism 12b receives light other than excitation light, included in reflected light (returning light) of the light emitted to body tissues of the subject 100 by the light source device 30. In the following explanation, reflected light of white light entering the spectroscopic prism 12b and then entering the image sensor 12c is sometimes simply referred to as white light.

The spectroscopic prism 12b disperses incident light into red (R) light, green (G) light, and blue (B) light. Then, the spectroscopic prism 12b focuses blue light onto the imaging surface of the image sensor 12c. Furthermore, the spectroscopic prism 12b focuses green light onto the imaging surface of the image sensor 12d. Moreover, the spectroscopic prism 12b focuses red light onto the imaging surface of the image sensor 12e.

Each of the image sensors 12c to 12e is, for example, a CMOS (complementary metal oxide semiconductor) image sensor. The image sensors 12c to 12e are provided such that imaging surface of each of the image sensors 12c to 12e substantially matches the image formation surface of the spectroscopic prism 12b. The pixels in each of the three (multiple) image sensors 12c to 12e output video signals when they receive the corresponding type of light.

Each of the image sensors 12c to 12e includes a plurality of pixels (imaging elements). The pixels are arranged in a matrix on an imaging surface. Due to drive control by the image-sensor control circuitry 12f, each pixel receives light to generate video signals (electric signals) and outputs generated video signals. For example, each pixel of the image sensor 12c receives blue light and then outputs B signals (B video signals). Furthermore, each pixel of the image sensor 12d receives green light and then outputs G signals (G video signals). Moreover, each pixel of the image sensor 12e receives red light and then outputs R signals (R video signals). For example, the camera head 12 including the image sensors 12c to 12e outputs RGB signals to the CCU 14 via the camera cable 13. Furthermore, the image sensors 12c to 12e output analog video signals.

Here, for example, the imaging device 10 according to the first embodiment is used for surgical operation conducted on the subject 100 with ICG (indocyanine green) fluorescence angiography. According to the first embodiment, ICG is administered into the subject 100. ICG is excited by excitation light output from an IR laser 30d and generates near-infrared fluorescence (hereafter, referred to as fluorescence) of approximately 800 to 850 nm. The fluorescence passes through the excitation-light cut filter 12a and is focused on the imaging surface of the image sensor 12e by the spectroscopic prism 12b. That is, the image sensor 12e receives fluorescence based on excitation light, thereby outputting R signals. In the following explanation, the image sensor 12e receives fluorescence and the imaging device 10 performs various operations; however, without providing the excitation-light cut filter 12a, the imaging device 10 may cause the image sensor 12e to receive reflected light of the excitation light and perform the same operation.

Each of the image sensors 12c to 12e is a rolling-shutter type image sensor that, on a frame-to-frame (image) basis, repeatedly performs a process to sequentially start to conduct exposure on at least every line starting from the first line of pixels to the last line and output video signals sequentially from the line for which exposure has been completed. Here, exposure means for example storage of electric charge in pixels.

Here, if the camera head 12 includes the image sensors 12c to 12e as described above, an increase in the resolution of images may be achieved by using a technique called half-pixel offset.

Furthermore, instead of the spectroscopic prism 12b and the three image sensors 12c to 12e, the camera head 12 may include a Bayer filter and a single image sensor. In this case, a Bayer filter is provided at the side of the imaging surface of the image sensor such that each pixel is opposed to any of the red filter, the green filter, and the blue filter. In this way, one pixel corresponds to one color filter. On a pixel by pixel basis, the image sensor outputs a video signal in the color of the filter that corresponds to the pixel. Furthermore, on a pixel by pixel basis, image processing circuitry 14c described later performs an estimation process to estimate video signals in the remaining two colors, which are not able to be directly obtained, on the basis of video signals output from neighboring pixels the pixel. As a result, the imaging device 10 may obtain RGB signals as video signals on a pixel by pixel basis.

The image-sensor control circuitry 12f controls driving of the image sensors 12c to 12e on the basis of a control signal output from control circuitry 14a described later and various synchronization signals output from timing-signal generation circuitry 14f described later. For example, on the basis of the control signal and the various synchronization signals, the image-sensor control circuitry 12f controls the image sensors 12c to 12e so as to apply appropriate gain (analog gain) to analog video signals (amplifies video signals) output from the image sensors to 12e and output the gained video signals to the CCU 14. Alternatively, if the image sensors 12c to 12e have an undepicted AD converter incorporated therein, the image-sensor control circuitry 12f controls the image sensors 2c to 12e so as to apply appropriate gain (digital gain) to digital video signals output from the image sensors 12c to 12e and output the gained video signals to the CCU 14.

The camera cable 13 is a cable that contains a signal line for transmitting and receiving video signals, control signals, and synchronization signals between the camera head 12 and the CCU 14.

The CCU 14 performs various types of image processing on video signals output from the camera head 12 to generate image data that represents images to be displayed on a display 101, and it outputs the image data to the display 101 connected to the CCU 14. Here, video signals on which various types of image processing has been conducted are image data that represents images to be displayed on the display 101.

The CCU 14 includes the control circuitry 14a, storage control circuitry 14b, the image processing circuitry 14c, image synthesis circuitry 14d, output circuitry 14e, timing-signal generation circuitry 14f, and memory circuitry 14g. Furthermore, if the image sensors 12c to 12e do not have an AD converter incorporated therein, the CCU 14 also includes an undepicted AD (analog to digital) converter, or the like. For example, the AD converter converts analog video signals output from the camera head 12 into digital video signals.

The control circuitry 14a controls various components of the imaging device 10. For example, the control circuitry 14a outputs a control signal to each circuitry, i.e., the image-sensor control circuitry 12f, the storage control circuitry 14b, the image processing circuitry 14c, the image synthesis circuitry 14d, the output circuitry 14e, and the timing-signal generation circuitry 14f, thereby controlling each circuitry. The control circuitry 14a performs a control process to control various components of the imaging device 10 by reading a control program for the imaging device 10, stored in the memory circuitry 14g, and executing the read control program. Alternatively, the control circuitry 14a includes an undepicted internal memory circuitry, and it executes a control program stored in the memory circuitry. The control circuitry 14a is implemented by using a processor such as an MPU (micro-processing unit).

The storage control circuitry 14b performs a control so as to store video signals, output from the camera head 12, in the memory circuitry 14g in accordance with control signals output from the control circuitry 14a and various synchronization signals output from the timing-signal generation circuitry 14f. Furthermore, the storage control circuitry 14b reads video signals stored in the memory circuitry 14g on a per-line basis in accordance with control signals and synchronization signals. Then, the storage control circuitry 14b outputs the read video signal of one line to the image processing circuitry 14c.

The image processing circuitry 14c performs various types of image processing on video signals output from the storage control circuitry 14b in accordance with control signals output from the control circuitry 14a and various synchronization signals output from the timing-signal generation circuitry 14f. Thus, the image processing circuitry 14c generates image data that represents an image to be presented on the display 101. That is, the image processing circuitry 14c generates images on the basis of video signals. For example, the image processing circuitry 14c applies gain (digital gain) to video signals output from the storage control circuitry 14b, thereby adjusting the brightness of an image. Furthermore, the image processing circuitry 14c may conduct a noise reduction process to reduce noise, an outline highlight process to highlight an outline, or the like, on video signals output from the storage control circuitry 14b. Then, the image processing circuitry 14c outputs video signals on which various types of image processing has been performed (image data that represents image to be presented on the display 101) to the image synthesis circuitry 14d.

On the basis of the control signal output from the control circuitry 14a and various synchronization signals output from the timing-signal generation circuitry 14f, the image synthesis circuitry 14d synthesizes video signals output from the image processing circuitry 14c to generate synthesis image data. Then, the image synthesis circuitry 14d outputs the synthesis image data to the display 101.

For example, the storage control circuitry 14b, the image processing circuitry 14c, and the image synthesis circuitry 14d are implemented by using a single processor such as a DSP (digital signal processor). Furthermore, for example, the storage control circuitry 14b, the image processing circuitry 14c, the image synthesis circuitry 14d, and the timing-signal generation circuitry 14f are implemented by using a single FPGA (field programmable gate array). Furthermore, the control circuitry 14a, the storage control circuitry 14b, the image processing circuitry 14c, and the image synthesis circuitry 14d may be implemented by using a single processing circuitry. This processing circuitry is implemented by using for example a processor.

The output circuitry 14e outputs synthesis image data, output from the image synthesis circuitry 14d, to the display 101. This allows the display 101 to present the synthesis image that is represented by the synthesis image data. Synthesis images are an example of images. The output circuitry 14e is implemented by using, for example, an HDMI (High-Definition Multimedia interface) (registered trademark) driver IC (integrated circuit) or an SDI (Serial Digital Interface) driver IC.

The timing-signal generation circuitry 14f integrally controls various types of timing, such as emission timing of light from the light source device 30, exposure timing of the image sensors 12c to 12e, output timing of video signals, or control timing of the memory circuitry 14g by the storage control circuitry 14b. The control circuitry 14a and the timing-signal generation circuitry 14f are an example of control unit.

The timing-signal generation circuitry 14f generates various synchronization signals such as horizontal synchronization signals, vertical synchronization signals, or other synchronization signals for synchronization of the entire imaging device 10 on the basis of clock signals generated by an undepicted oscillation circuitry. Then, the timing-signal generation circuitry 14f outputs various generated synchronisation signals to each circuitry, i.e., the image-sensor control circuitry 12f, the control circuitry 14a, the storage control circuitry 14b, the image processing circuitry 14c, the image synthesis circuitry 14d, and the output circuitry 14e.

Furthermore, the timing-signal generation circuitry 14f generates light-source control signals on the basis of clock signals and control signals output from the control circuitry 14a. Light-source control signals are control signals for controlling light output from the light source device 30 and synchronizing the entire imaging system 1. Furthermore, the timing-signal generation circuitry 14f outputs generated light-source control signals to the light source device 30.

For example, the waveform of light-source control signals is a square wave, and light-source control signals have two levels (states), a high level and a low level. For example, light-source control signals are control signals that cause a white LED 30b to output white light and cause the IR laser 30d to output excitation light while in a high level and that cause the white LED 30b to be turned off and cause the IR laser 30d to stop outputting excitation light while in a low level.

The memory circuitry 14g is implemented by using for example a semiconductor memory device such as a RAM (random access memory) or a flash memory, a hard disk, or an optical disk. The memory circuitry 14g stores various programs. For example, the memory circuitry 14g stores control programs executed by the control circuitry 14a. Furthermore, the storage control circuitry 14b temporarily stores video signals in the memory circuitry 14g.

The light source device 30 outputs white light or excitation light in accordance with light-source control signals. The light source device 30 includes drive circuitry 30a, the white LED (light emitting diode) 30b, drive circuitry 30c, and the IR laser 30d.

The drive circuitry 30a conducts drive control to drive the white LED 30b so as to be turned on in accordance with a light-source control signal output from the timing-signal generation circuitry 14f. The white LED 30b outputs white light due to the drive control by the drive circuitry 30a. White light is for example visible light. Furthermore, white light is an example of the light. Moreover, white light is an example of second light.

The drive circuitry 30c conducts drive control to drive the IR laser 30d so as to output excitation light from the IR laser 30d in accordance with light-source control signals output from the timing-signal generation circuitry 14f. The IR laser 30d outputs excitation light due to drive control by the drive circuitry 30c. Furthermore, as described above, excitation light is cut by the excitation-light cut filter 12a. Furthermore, fluorescence (fluorescence based on excitation light), which is output from ICG after ICG is excited by excitation light, is passed through the excitation-light cut filter 12a and is received by the image sensor 12e. The excitation light is an example of light. Furthermore, the excitation light is an example of first light.

The optical fiber 31 guides white light and excitation light from the light source device 30 to the distal end of the scope 11 and causes them to be output from the distal end of the scope 11.

An example of the configuration imaging device 10 in the imaging system 1 according to the first embodiment is explained above. Here, an imaging device according to a comparative example is explained. The imaging device according to the comparative example includes a rolling-shutter type image sensor.

Figure 2:
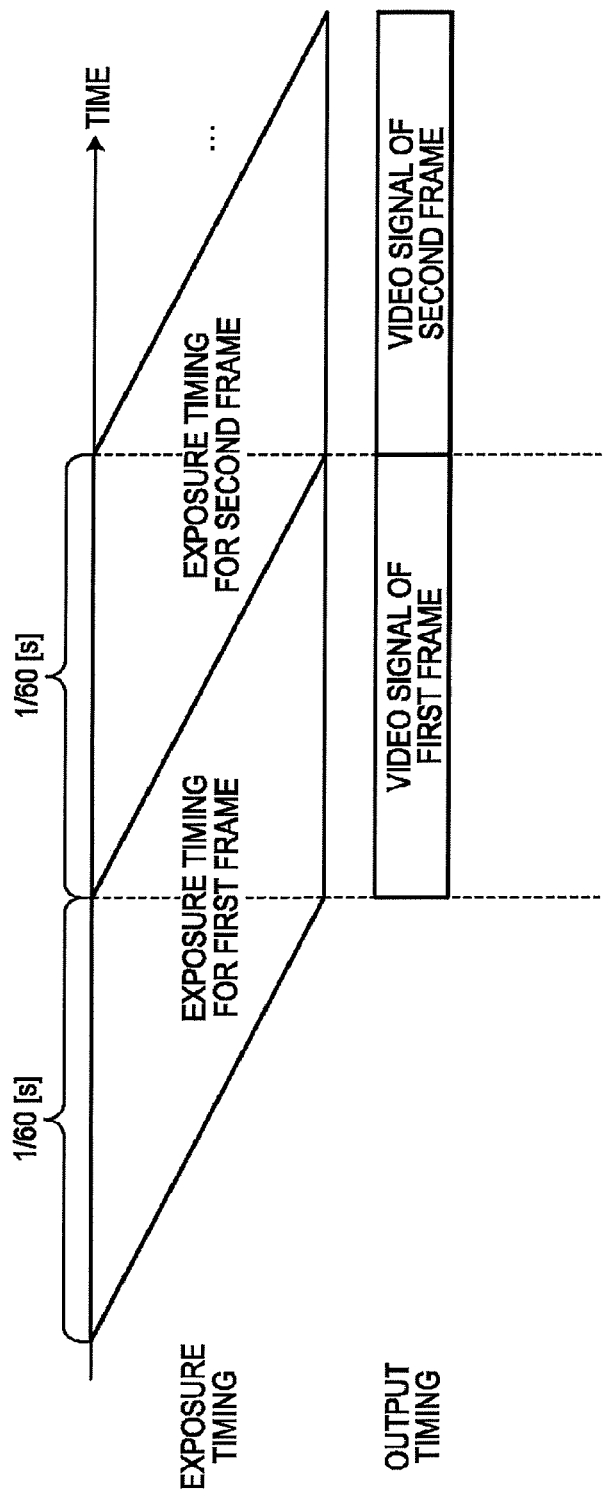
FIG. 2 is a diagram that illustrates an example of operation of the imaging device according to a comparative example.

FIG. 2 is a diagram that illustrates an example of operation of the imaging device according to the comparative example. FIG. 2 illustrates an example of the relationship between the exposure timing of each line of pixels included in the image sensor of the imaging device according to the comparative example and the output timing of video signals output from the image sensor. As illustrated in FIG. 2, in the imaging device according to the comparative example, during imaging for the first frame, exposure is sequentially started on a per-line basis from the first line of pixels to the last line. With the imaging device according to the comparative example, an exposure period is $\frac{1}{60}$ [s]. Here, the exposure period refers to, for example, the period from when a pixel starts to store an electric charge until it ends.

Furthermore, as illustrated in FIG. 2, with the imaging device according to the comparative example, video signals are sequentially output starting from the line for which exposure has been completed. That is, video signals are sequentially output from each line starting from the first line to the last line. Here, with the imaging device according to the comparative example, the period (read period) during which video signals of one frame are output from the image sensor is 1/60 [s], which is the same as the exposure period. Furthermore, as illustrated in FIG. 2, the sane process is performed for the second and subsequent frames.

With the imaging device according to the comparative example, for all the lines of pixels in the image sensor, the period (light receiving period) during which light is received is the same period as the exposure period. Therefore, the light receiving period of each line from the first line to the last line is sequentially shifted in the direction of a time axis. Thus, with the imaging device according to the comparative example, as the light receiving period of each line is different, distortion sometimes occurs in images. In this case, there is a problem in that the image quality is not sufficient for observation to users such as doctors who observe images.

Thus, with the above-described configuration, the imaging device 10 according to the first embodiment conducts the following operation to ensure the image quality and the frame rate that are sufficient for user's observation.

According to the present embodiment, the exposure period of the image sensors 12c to 12e is one-half of the period during which video signals of one frame are output from the imaging device 10 to the display 101. Furthermore, the control circuitry 14a performs a control so as to cause the pixels in each of the image sensors 12c to 12e to receive light during only the blanking period or the period centered on the blanking period. For example, the control circuitry 14a outputs a control signal to the image-sensor control circuitry 12f so as to cause the image-sensor control circuitry 12f to perform the above control.

Here, the control circuitry 14a performs control so as to cause the pixels receive light during a period that is less than the read period. The read period refers to, for example, the period during which video signals of one frame are output from the image sensors 12c to 12e. Furthermore, the read period refers to, for example, the period from when the output of video signals from the first line in one frame is started until the output of video signals from the last line is finished.

Furthermore, according to the present embodiment, the blanking period refers to, for example, a period that corresponds to the period from when the output of video signals from the last line in the image sensors 12c to 12e is finished with respect to imaging for the n-th (n is a positive integer) frame until the output of video signals from the first line in the image sensors 12c to 12e is started with respect to imaging for the (n+1)-th frame.

According to the present embodiment, the frame rate of video signals (image) output from the imaging device 10 to the display 101 is A [fps (frame per second)]. In this case, image sensors that enable a read period of 1/(M·A) are used as the image sensors 12c to 12e of the imaging device 10. That is, image sensors capable of outputting video signals from each line at an interval of 1/(M·k·A) [s] are used as the image sensors 12c to 12e. Here, "M" is a number larger than 1, and "k" is the number of lines of pixels in each of the image sensors 12c to 12e. An explanation is given below of a case where for example M=2; however, M may be a number different from 2 and larger than 1.

Furthermore, the control circuitry 14a outputs, to the image-sensor control circuitry 12f, a control signal for causing the image sensors 12e to output video signals of one frame in the read period 1/(2A) [s] that is shorter than the exposure period 1/A [s].

An explanation is given below of a case where, for example, A=60. That is, in the following explanation, the exposure period and the period during which video signals of one frame are output from the imaging device 10 to the display 101 are the same, 1/60 [s], and the read period is 1/120 [s].

Figure 3:
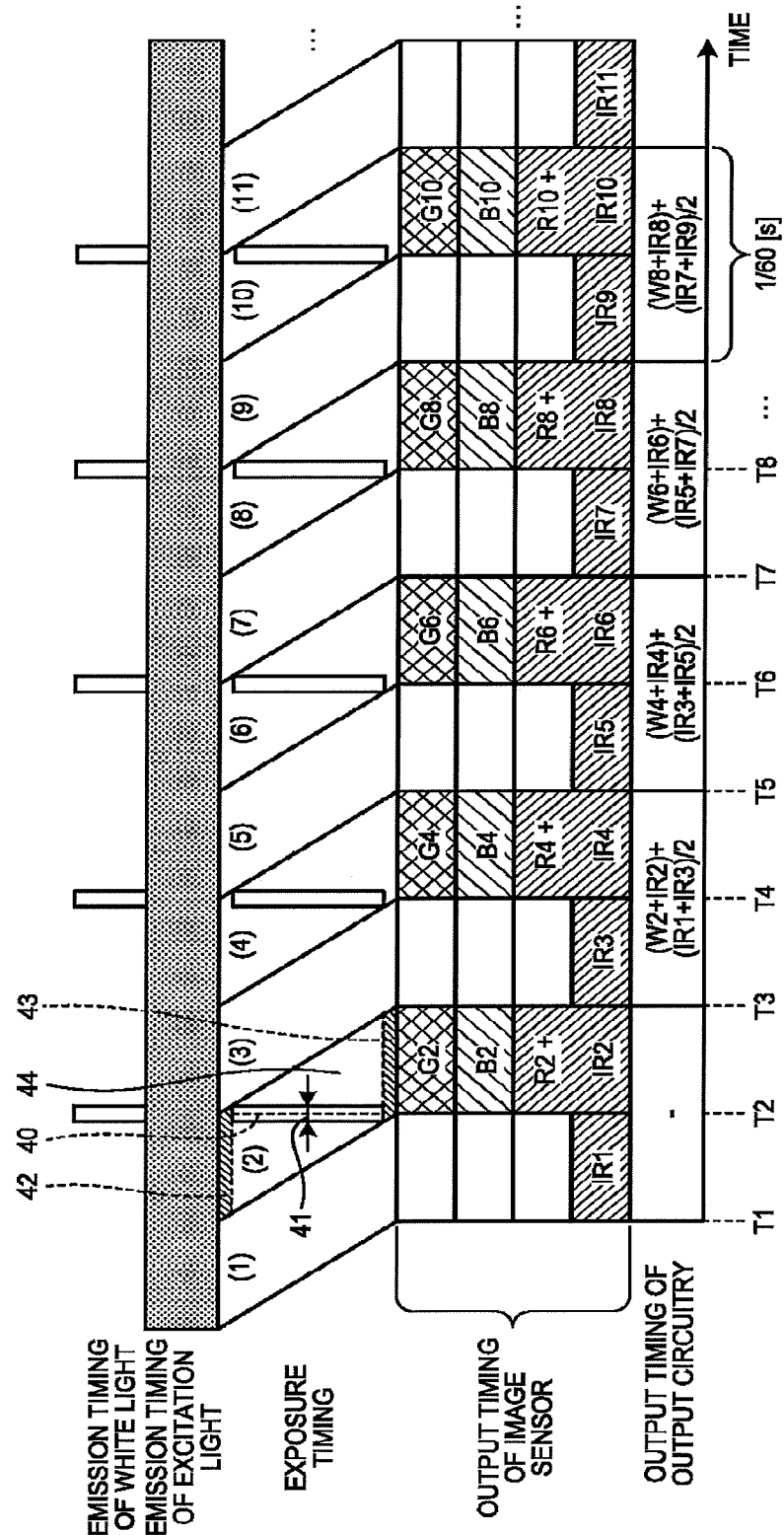
FIG. 3 is a diagram that illustrates an example of imaging operation of the imaging device according to the first embodiment.

FIG. 3 is a diagram that illustrates an example of imaging operation of the imaging device 10 according to the first embodiment. FIG. 3 illustrates an example of the relationship among the emission timing of white light and excitation light output from the light source device 30 according to the first embodiment, the exposure timing of each line of pixels included in the image sensors 12c to 12e of the imaging device 10, the output timing of video signal output from the image sensors 12c to 12e, and the output timing of video signals output from the output circuitry 14e. In FIG. 3, the horizontal axis indicates a time.

Furthermore, in FIG. 3, for simplification of the drawing, two different times, i.e., the time (timing) when the output of a video signal from the last line in the image sensors 12c to 12e is finished with respect to imaging for the n-th frame and the time when the output of a video signal from the first line in the image sensors 12c to 12e is started with respect to imaging for the (n+1)-th frame, are indicated as the same "Tp(p=n+1)". In actuality, as described above, a blanking period exists as the period from when the output of a video signal from the last line in the image sensors 12c to 12e is finished with respect to imaging for the n-th frame to when the output of a video signal from the first line in the image sensors 12c to 12e is started with respect to imaging for the (n+1)-th frame.

In FIG. 3, (n) indicates the exposure timing during imaging for the n-th frame. Here, n is a positive integer as described above. According to the first embodiment, the amount of fluorescence generated due to emission of excitation light is smaller than the amount of reflected light of white light output from the white LED 30b. For example, the amount of fluorescence is vanishingly smaller than the amount of reflected light of white light. Therefore, it is considered that the effect of fluorescence images obtained from fluorescence based on excitation light is significantly small on color images obtained from white light. For this reason, according to the first embodiment, excitation light is always (continuously) output from the IR laser 30d. Therefore, the amount of fluorescence received by the image sensor 12e is large as compared with a case where excitation light is not always output from the IR laser 30d. Thus, fluorescence receiving sensitivity may be improved, and a decrease in the brightness of images due to a shortage in the amount of light may be prevented.

In FIG. 3, if n is an odd number, IRn denotes the R signal output from the image sensor 12e with regard to imaging for the n-th frame. That is, if n is an odd number, IRn denotes the R signal output from the image sensor 12e that has received fluorescence based on excitation light.

In FIG. 3, if n is an even number, Gn denotes the G signal output from the image sensor 12d with regard to imaging for the n-th frame. Furthermore, if n is an even number, En denotes the B signal output from the image sensor 12c with regard to imaging for the n-th frame. Furthermore, if n is an even number, "Rn+IRn" denotes the R signal output from the image sensor 12e with regard to imaging for the n-th frame. Specifically, "Rn+IRn" denotes the R signal output from the image sensor 12e that has simultaneously received white light and fluorescence based on excitation light with regard to imaging for the n-th frame. Furthermore, "Wn+IRn" denotes the RGB signal output from the image sensors 12c to 12e with regard to imaging for the n-th frame. That is, "Wn+IRn" is a synthesis signal of Gn, En, and Rn.

In the example of FIG. 3, before imaging for the first frame is started or when imaging for the first frame is started, the control circuitry 14a outputs, to the timing-signal generation circuitry 14f, a control signal for outputting a first light-source control signal. The first light-source control signal is a control signal for causing the IR laser 30d to continuously output excitation light.

The timing-signal generation circuitry 14f outputs, to the drive circuitry 30c, the first light-source control signal for continuously outputting excitation light on the basis of the above-described control signal output from the control circuitry 14a. The drive circuitry 30c causes the IR laser 30d to continuously output excitation light on the basis of the first light-source control signal output from the timing-signal generation circuitry 14f.

As illustrated in FIG. 3, during imaging for the first frame, exposure is sequentially started on a per-line basis, starting from the first line of pixels to the last line. With respect to imaging for the first frame, fluorescence based on excitation light is received by the image sensor 12e, and the image sensor 12e outputs the R signal (IR1) during the read period $1/120$ [s] from a time T1 to a time T2. That is, the image sensor 12e outputs a video signal from each line at an interval of $1/(120\ k)$ [s]. Here, the time T1 is a time when the output of a video signal from the first line is started during the first name. The time T2 is a time when the output of a video signal from the last line is finished with regard to the first frame.

A specific control method is explained; the control circuitry 14a outputs, to the image-sensor control circuitry 12f, the control signal for causing the image sensor 12e to output video signals of the first frame during the read period $1/120$ from the time T1. Specifically, the control circuitry 14a outputs, to the image-sensor control circuitry 12f, the control signal for causing the image sensor 12e to sequentially start to output a video signal from each line at an interval of $1/(120\ k)$ [a] from the time T1.

The image-sensor control circuitry 12f controls the image sensor 12e so as to be driven on the basis of the control signal. As a result, the image sensor 12e outputs video signals of all the lines (k lines) during the read period $1/120$ [s] from the time T1 to the time T2.

Then, each time a video signal output from each line of the image sensor 12e is input with respect to imaging for the first frame, the storage control circuitry 14b temporarily stores the video signal output from each line in the memory circuitry 14g. Here, from the time 11 to the time T2, the storage control circuitry 14b stores a video signal output from each line, sequentially from the first line to the last line, in the memory circuitry 14g. Video signals stored with respect to imaging for the first frame as described above are stored in the memory circuitry 14g until at least a time T5.

Next, as illustrated in FIG. 3, during imaging for the second frame, exposure is sequentially started on a per-line basis from the first line of pixels in each of the image sensors 12c to 12e to the last line.

Here, the period from the time 12 when the output of a video signal from the last line is finished with regard to imaging for the first frame to the time when the output of a video signal from the first line is started with regard to imaging for the second frame corresponds to a blanking period 40 as illustrated in FIG. 3. Here, as the blanking period 40 is a relatively short period as compared with an exposure period, or the like, it is indicated by a single dotted line in FIG. 3; however, in actuality, it is a period that has a certain width in the direction of a time axis.

According to the present embodiment, as illustrated in FIG. 3, during imaging for the second frame, white light is output from the white LED 30b during only the blanking period 40 or a period 41 centered on the blanking period 40. For example, with regard to imaging for the second frame, if white light is output during only the period 41 centered on the blanking period 40, at least one line 42 at the side of the first line and at least one line 43 at the side of the last line among all the lines of pixels in the image sensors 12c to 12e are irradiated with white light during only a time that is shorter than the period 41.

Furthermore, white light may be output from the white LED 30b within the blanking period 40. In this case, white light may be output not only during the period centered on the center of the blanking period 40 but also at any timing within the blanking period 40. Furthermore, for example, the period 41 is a period longer than the blanking period 40, and it includes the blanking period 40 and includes periods before and after the blanking period 40. The blanking period, a period within the blanking period, and the period centered on the blanking period are examples of a period based on the blanking period.

Furthermore, as illustrated in FIG. 3, the light receiving period for receiving white light is substantially the same for one or more lines 44 except for the line 42 and the line 43 among all the lines. That is, the light receiving period of the line 44 is different from those of the line 42 and the line 43. For this reason, the imaging device 10 masks the image obtained in accordance with video signals output from the line 42 and the line 43 and sets the area of image obtained in accordance with a video signal output from the line 44 as an effective image area. This allows the display 101 to present images by masking parts where uneven brightness likely to occur. Therefore, the occurrence of distortion in images may be prevented. Thus, with the imaging device 10 according to the first embodiment, it is possible to ensure the image quality sufficient for observation to users such as doctors who observe images.

Furthermore, as illustrated in FIG. 3, in imaging for the third frame, at least one line at the side of the first line among all the lines of pixels receives not only fluorescence based on excitation light but also white light during an exposure period. Furthermore, during imaging for the first frame, at least one line at the side of the last line among all the lines of pixels receives not only fluorescence based on excitation light but also white light during an exposure period. As components of white light are thus included, it is difficult to generate fluorescence images composed of only fluorescence components with a desired image quality by using video signals output from the lines that receive white light as well as fluorescence.

Therefore, in the same manner during imaging for the first frame and imaging for the third frame, the imaging device 10 according to the first embodiment masks images obtained in accordance with video signals output from the line 42 and the line 43 and sets the area of image obtained in accordance with a video signal output from the line 44 as an effective image area. This allows the display 101 to present images by masking parts whose image quality may be undesirable.

Therefore, in this aspect, too, with the imaging device 10 according to the first embodiment, it is possible to ensure the image quality sufficient for observation to users such as doctors who observe images.

Here, an explanation is given of an example of the reason why the period 41 is a period centered on the blanking period. If the period 41 is not a period centered on the blanking period, there is a possibility that, with regard to images whose ends are masked, the size of the masked area at one end side is different from the size of the masked area at the other end side and users observing the images may feel uncomfortable.

However, if the period 41 is a period centered on the blanking period, the size of the masked area at one end side is substantially the same as the size of the masked area at the other end side, and user's uncomfortable feeling may be prevented.

Furthermore, the image sensors 12c to 12e output video signals (RGB signals) from ail the lines (k lines) during the read period 1/120 [s] from the time T2 to a time T3.

A specific control method is explained. The control circuitry 14a outputs, to the image-sensor control circuitry 12f, the control signal for causing the image sensors 12c to 12e to output video signals during the read period 1/120 [s] from the time T2. Specifically, the control circuitry 14a outputs, to the image-sensor control circuitry 12f, the control signal for causing the image sensors 12c to 12e to start to output a video signal from each line at an interval of 1/(120 k) [s] from the time T2.

In accordance with the control signal, the image-sensor control circuitry 12f controls the image sensors 12c to 12e so as to be driven. As a result, the image sensor 12c outputs video signals (B signals) from all the lines (k lines) during the read period 1/120 [s] from the time T2 to the time T3. Furthermore, the image sensor 12d outputs video signals (G signals) from all the lines (k lines) during the read period 1/120 [s] from the time T2 to the time T3. Moreover, the image sensor 12e outputs video signals (R signals (R2+IR2)) from all the lines (k lines) with regard to imaging for the second frame during the read period 1/120 [s] from the time T2 to the time T3.

Then, each time a video signal output from each line of the image sensor 12c is input from the time T2 to the time T3, the storage control circuitry 14b temporarily stores the video signal output from each line in the memory circuitry 14g. Furthermore, each time a video signal output from each line of the image sensor 12d is input from the time T2 to the time T3, the storage control circuitry 14b temporarily stores the video signal output from each line in the memory circuitry 14g. Moreover, each time a video signal output from each line of the image sensor 12e is input from the time T2 to the time T3, the storage control circuitry 14b temporarily stores the video signal output from each line in the memory circuitry 14g. Here, with regard to imaging for the second frame, a video signal output from each line, sequentially from the first line to the last line, is stored in the memory circuitry 14g from the time T2 to the time T3. In this manner, video signals stored with regard to imaging for the second frame are stored in the memory circuitry 14g until at least the time T5.

Then, as illustrated in FIG. 3, during imaging for the third frame, exposure is sequentially started on a per-line basis from the first line of pixels to the last line. With respect to imaging for the third frame, the image sensor 12e receives fluorescence based on excitation light, and the image sensor 12e outputs an R signal (IR3) during the read period 1/120 from the time T3 to a time T4. That is, a video signal is output from each line of the image sensor 12e at an interval of 1/(120 k) [s]. Here, the time T3 is a time when the output of a video signal from the first line is started with regard to imaging for the third frame. The time T4 is a time when the output of a video signal from the last line is finished with regard to imaging for the third frame.

A specific control method is explained; the control circuitry 14a outputs, to the image-sensor control circuitry 12f, the control signal for causing the image sensor 12e to output a video signal during the read period 1/120 [s] from the time T3. Specifically, the control circuitry 14a outputs, to the image-sensor control circuitry 12f, the control signal for causing the image sensor 12e to start to output a video signal from each line at an interval of 1/(120 k) [s] from the time T3.

The image-sensor control circuitry 12f controls the image sensor 12e so as to be driven in accordance with the control signal. As a result, the image sensor 12e outputs video signals from all the lines (k lines) during the read period 1/120 [s] from the time T3 to the time T4.

Then, each time a video signal output from each line of the image sensor 12e is input with regard to imaging for the third frame, the storage control circuitry 14b temporarily stores a video signal output from each line in the memory circuitry 14g. Here, with regard to imaging for the third frame, a video signal output from each line, sequentially from the first line to the last line, is stored in the memory circuitry 14g from the time T3 to the time T4. In this manner, video signals stored with regard to imaging for the third frame are stored in the memory circuitry 14g until at least a time 17.

Here, an explanation is given of a process indicated by "(W2+IR2)+(IR1+IR3)/2" in FIG. 3. In the stage at the time T3, the memory circuitry 14g stores the video signal (IR1) of the first frame and the video signal (W2+IR2) of the second frame. Furthermore, as described above, the video signal (IR3) of the third frame starts to be stored in the memory circuitry 14g at the time 13.

Furthermore, according to the present embodiment, the imaging device 10 synthesizes the video signal (IR1) of the first frame, the video signal (W2+IR2) of the second frame, and the video signal (IR3) of the third frame and outputs it to the display 101.

Here, an explanation is simply given of a case where each time the video signal (IR3) is output from each line of the image sensor 12e with regard to imaging for the third frame, the imaging device 10 synthesizes the video signal (IR3) output from each line, the video signal (IR1) output from each line, and the video signal (W2+IR2) output from each line of the image sensors 12c to 12e and outputs a synthesis image to the display 101. In this case, a synthesis image of video signals output from all the lines is output to the display 101 in 1/120 [s].

Here, there is a period where no video signals are output to the display 101 during 1/120 [s] from when a video signal of the last line is output to the display 101 with regard to imaging for a certain frame until a video signal of the first line is output to the display 101 with regard to imaging for the subsequent frame. Periods where no video signals are output are periods where images presented on the display 101 are not updated. For this reason, the period of 1/120 [s] where images are updated and the period of 1/120 [s] where images are not updated are alternately arranged. In this case, as images are not updated at a constant frequency, the display 101 sometimes cannot respond to these inputs.

Therefore, according to the present embodiment, for updates to images at a constant frequency, the frame rate of video signals of one frame output from the output circuitry 14e to the display 101 is set to 60 [fps]. That is, there is a reduction in the period from the output of a video signal of the last line with regard to imaging for a certain frame until the output of a video signal of the first line with regard to imaging for the subsequent frame.

Therefore, the storage control circuitry 14b sequentially reads, from the memory circuitry 14g, the video signal (IR1) output from each line with regard to imaging for the first frame, the video signal (W2+IR2) output from each line with regard to imaging for the second frame, and the video signal (IR3) output from each line with regard to imaging for the third frame at an interval of 1/(60 k) [s] from the time T3. For example, the storage control circuitry 14b reads the video signal (IR1) and the video signal (IR3) output from the m-th line of the image sensor 12e and the video signal (W2+IR2) output from the m-th line of the image sensors 12c to 12e. Here, m is a positive integer. Then, the storage control circuitry 14b outputs, to the image processing circuitry 14c, the video signal (IR1) and the video signal (IR3) output from the m-th line of the image sensor 12e and the video signal (W2+IR2) output from the m-th line of the image sensors 12c to 12e.

Then, the image processing circuitry 14c performs various types of image processing on the video signal (IR1) and the video signal (IR3) output from the m-th line of the image sensor 12e and the video signal (W2+IR2) output from the m-th line of the image sensors 12c to 12e and outputs it to the image syntheses circuitry 14d.

An explanation is given below of an example of various types of image processing performed by the image processing circuitry 14c. For example, the image processing circuitry 14c applies digital gain to the video signal (IR1) output from the m-th line of the image sensor 12e with regard to imaging for the first frame. The image processing circuitry 14c applies the digital gain and the above-described analog gain to amplify the video signal (IR1), output from the m-th line of the image sensor 12e, up to for example 30-fold.

In the same manner, the image processing circuitry 14c applies digital gain to the video signal (IR3) output from the m-th line of the image sensor 12e with regard to imaging for the third frame. With the combination of the digital gain and the above-described analog gain, the image processing circuitry 14c amplifies the video signal output from the m-th line of the image sensor 12e up to for example 30-fold.

Furthermore, the image processing circuitry 14c does not apply digital gain or analog gain to the m-th video signal (W2+IR2) output from the image sensors 12c to 12e with regard to imaging for the second frame.

Furthermore, the image processing circuitry 14c according to the present embodiment masks the images obtained in accordance with the video signals output from the line 42 and the line 43 described above. Furthermore, the image processing circuitry 14c sets the area of image obtained in accordance with the video signal output from the line 44 described above as an effective image area.

Figure 4A:
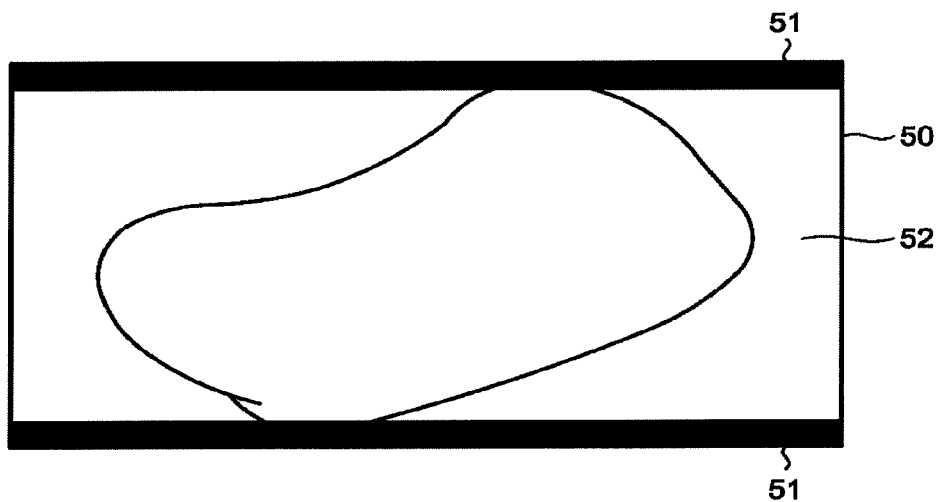
FIG. 4A is a diagram that illustrates an example of image processing conducted by image processing circuitry.

FIG. 4A is a diagram that illustrates an example of image processing conducted by the image processing circuitry 14c. As illustrated in the example of FIG. 4A, for example, the image processing circuitry 14c generates a color image 50 where the images obtained in accordance with the video signals (W2+IR2) output from the line 42 and the line 43 described above are replaced with images 51 in black and the area of image obtained in accordance with the video signal (W2+IR2) output from the line 44 described above is set as an effective image area 52.

The color image 50 illustrated in the example of FIG. 4A is an example of the color image in a case where pixels of the image sensors 12c to 12e receive light during only the period that is centered on a blanking period with an addition of 1/1200 [s] to the blanking period. On the color image 50, 10% of the entire area of the color image 50 is masked.

In the same manner, the image processing circuitry 14c generates a fluorescence image where the images obtained in accordance with the video signals (IR1) output from the line 42 and the line 43 described above are replaced with images in black and the area of image obtained in accordance with the video signal (IR1) output from the line 44 described above is set as an effective image area. Furthermore, the image processing circuitry 14c generates a fluorescence image where the images obtained in accordance with the video signals (IR3) output from the line 42 and the line 43 described above are replaced with images in black and the area of image obtained in accordance with the video signal (IR3) output from the line 44 described above is set as an effective image area.

The image synthesis circuitry 14d generates a synthesis image by synthesizing the video signal (IR1) output from each line of the image sensor 12e with regard to imaging for the first frame and the video signal (IR3) output from each line of the image sensor 12e with regard to imaging for the third frame. For example, the image synthesis circuitry 14d synthesizes the video signal (IR1) and the video signal (IR3) to generate a synthesis image ((IR1+IR3)/2).

Then, the image synthesis circuitry 14d extracts for example part of the synthesis image ((IR1+IR3)/2) with luminance equal to or more than a threshold. Then, the image synthesis circuitry 14d generates a marker that has the same position and area as the extracted part and that has a predetermined color (e.g., highly intense green) assigned thereto. Then, the image synthesis circuitry 14d superimposes the generated marker on the video signal (W2+IR2) output from each line with regard to imaging for the second frame, thereby generating a synthesis image (W2+IR2+(IR1+IR3)/2). Then, the image synthesis circuitry 14d outputs the generated synthesis image (W2+IR2+(IR1+IR3)/2) to the output circuitry 14e. The image synthesis circuitry 14d generates a synthesis image by using a color image and multiple (two) fluorescence images generated before and after the color image.

For example, the color tone of color images obtained as in-vivo images of the subject 100 is a reddish color tone in whole. For this reason, if red is assigned to a maker, for example, the marker is not noticeable. Therefore, green that is a complementary color of red is assigned to the marker so that the marker is noticeable.

Furthermore, instead of the marker, the image synthesis circuitry 14d may generate a synthesis image by extracting an outline component from a fluorescence image obtained due to fluorescence and superimposing the extracted outline component on a color image.

The image synthesis circuitry 14d performs the above process on video signals output from all the lines. Specifically, the image synthesis circuitry 14d outputs a synthesis image of video signals output from all the lines to the output circuitry 14e during the period of 1/60 [s] from the time T3 to the time T5. Thus, as indicated by "W2+IR2+(IR1+IR3)/2" in FIG. 3, the output circuitry 14e outputs an synthesis image of video signals from all the lines to the display 101 during the period of 1/60[s] from the time T3 to the time T5. Hence, the synthesis image presented on the display 101 is updated at an interval of 1/60 [s].

For the fourth and subsequent frames, imaging operation is repeatedly conducted in the same manner as the imaging operation described with regard to imaging for the first frame, imaging for the second frame, and imaging for the third frame. Therefore, the control circuitry 14a causes the light source device 30 to continuously output excitation light and causes the light source device 30 to output white light, which is a different type from excitation light, once in two frames in synchronization with the blanking period 40 or the period 41. The image processing circuitry 14c generates fluorescence images in accordance with video signals generated by pixels of the image sensor 12e after receiving fluorescence based on excitation light. Here, video signals generated by pixels of the image sensor 12e after receiving fluorescence are an example of a first electric signal. Furthermore, fluorescence images are an example of a first image.

Furthermore, the image processing circuitry 14c generates color images in accordance with video signals generated by pixels of the image sensors 12c to 12e after simultaneously receiving fluorescence and white light. Here, video signals generated by pixels of the image sensors 12c to 12e after simultaneously receiving fluorescence and white light are an example of a second electric signal. Furthermore, color images are an example of a second image.

The image synthesis circuitry 14d generates synthesis images by using fluorescence images and color images. For example, the image processing circuitry 14c and the image synthesis circuitry 14d are an example of an image generating unit.

FIG. 48 is a diagram that illustrates an example of the synthesis image. FIG. 48 illustrates an example of the synthesis image where a marker 53 is superimposed on the color image 50 where part that is likely to have uneven brightness is masked. This allows users to easily observe for example the marker 53 that is a notable area. Furthermore, it is possible for users to obtain information on the marker 53 while observing the color image 50 that is a color image with contents that are actually recognizable by persons.

Furthermore, with regard to the color image 50, exposure timing is identical. Therefore, with the imaging device 10 according to the first embodiment, the occurrence of image distortion may be prevented. Thus, with the imaging device 10 according to the first embodiment, it is possible for users such as doctors who observe images to ensure the image quality sufficient for observation.

Figure 4B:
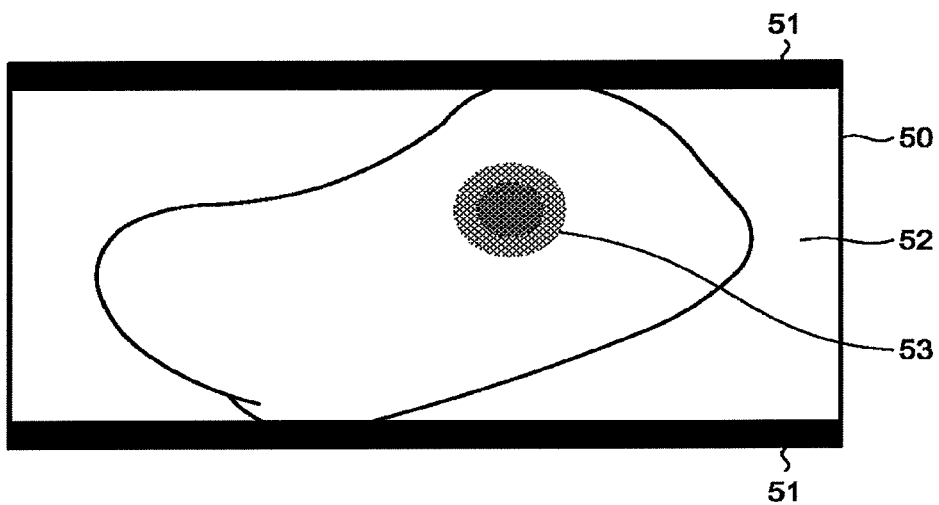
FIG. 4B is a diagram that illustrates an example of synthesis image.

As illustrated in FIG. 4B, the image processing circuitry 14c sets, in the synthesis image, the effective image area 52 except for at least the synthesis image's edge portions that correspond to the first line and the last line. Furthermore, the image processing circuitry 14c and the image synthesis circuitry 14d generate the synthesis image where the area other than the effective image area 52 is replaced with the image (different image) 51 in black.

Here, an explanation is given of a case where the imaging target moves in a predetermined direction on a synthesis image. Furthermore, an explanation is given of a case where the marker obtained from the fluorescence image (IR1) is superimposed on the color image (W2+IR2) to generate the synthesis image (W2+IR2+IR1). In this case, as the imaging target moves, the position of the center of gravity of the marker is located backward in terms of time relative to position of the center of gravity of the imaging target rendered on the color image (W2+IR2).

Next, an explanation is given of a case where the marker obtained from the fluorescence image (IR3) is superimposed on the color image (W2+IR2) to generate the synthesis image (W2+IR2+IR3). In this case, as the imaging target moves, the position of the center of gravity of the marker is located forward in terms of time relative to the position of the center of gravity of the imaging target rendered on the color image (W2+IR2).

Here, according to the present embodiment, the marker obtained from the synthesis image ((IR1+TR3)/2) of the fluorescence image (IR1) and the fluorescence image (IR3) is superimposed on the color image (W2+IR2) to generate the synthesis image (W2+TR2+(TR1+IR3)/2). According to the present embodiment, even if the imaging target moves, the marker obtained from the synthesis image ((IR1+IR3)/2) of the fluorescence image (IR1) and the fluorescence image (IR3), which are captured at imaging timings before and after the imaging timing of the color image (W2+IR2) by substantially the same time, is superimposed on the color image (W2+IR2). For this reason, the difference between the position of the center of gravity of the color image (W2+IR2) and the position of the center of gravity of the synthesis image ((IR1+IR3)/2) is relatively small. Therefore, it is possible to reduce misalignment of the position of the center of gravity of the marker relative to the position of the center of gravity of the imaging target rendered on the synthesis image (W2+IR2+(IR1+IR3)/2). Thus, according to the first embodiment, it is possible to reduce user's uncomfortable feelings caused by the synthesis image (W2+IR2+(IR1+IR3)/2) due to movements.

Figure 5:
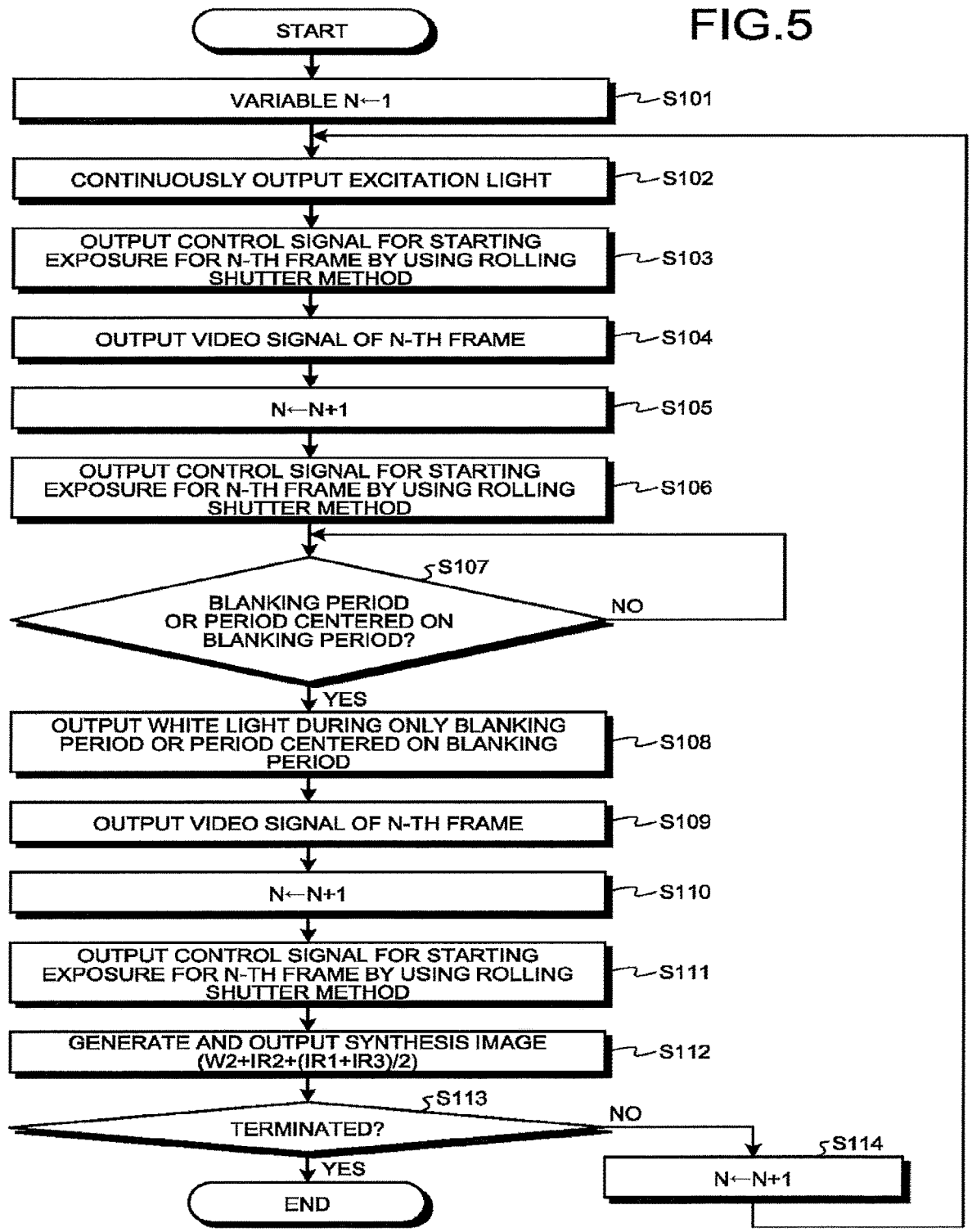
FIG. 5 is a flowchart that illustrates the flow of a control process according to the first embodiment.

Next, an explanation is given of a control process performed by the control circuitry 14a according to the first embodiment. FIG. 5 is a flowchart that illustrates the flow of a control process according to the first embodiment. This control process is performed by the control circuitry 14a when an undepicted input device, such as a mouse or keyboard that receives commands from users, inputs a command to the CCU 14 so as to start imaging on the inside of the body of the subject 100.

As illustrated in FIG. 5, the control circuitry 14a sets "1" as the variable N (Step S101). Then, the control circuitry 14a outputs, to the timing-signal generation circuitry 14f, a control signal for outputting a light-source control signal that causes the IR laser 30d to continuously output excitation light (Step 102). Then, in order to start imaging for the N-th frame, the control circuitry 14a outputs, to the image-sensor control circuitry 12f, a control signal for starting exposure for the N-th frame by using the rolling shutter method (Step S103).

Then, the control circuitry 14a outputs, to the image-sensor control circuitry 12f, the control signal for causing the image sensor 12e to output video signals during the read period 1/120 [s] from the time when the output of a video signal of the first line of pixels of the image sensor 12e is started with respect to imaging for the N-th frame (Step S104). Here, each time a video signal output from each line of the image sensor 12e is input at Step S104, the storage control circuitry 14b temporarily stores the video signal output from each line in the memory circuitry 14g.

Then, the control circuitry 14a increments the value of the variable N (Step S105). Then, in order to start imaging for the N-th frame, the control circuitry 14a outputs, to the image-sensor control circuitry 12f, the control signal for starting exposure for the N-th frame by using a rolling shutter method (Step S106).

The control circuitry 14a determines whether the current time is a blanking period or a period centered on the blanking period (Step S107). If the current time is not a blanking period or a period centered on the blanking period (Step S107; No), the control circuitry 14a makes a determination again at Step 3107.

Conversely, if the current time is a blanking period or a period centered on the blanking period (Step S107; Yes), the control circuitry 14a performs the following process. Specifically, the control circuitry 14a outputs, to the timing-signal generation circuitry 14f, the control signal for outputting the light-source control signal that causes the white LED 30b to output white light during only the blanking period or the period centered on the blanking period (Step S108).

Then, the control circuitry 14a outputs, to the image-sensor control circuitry 12f, the control signal for outputting video signals to the image sensors 12c to 12e during the read period ¹/₁₂₀ from the time when the output of a video signal from the first line is started (Step S109). Here, each time a video signal output from each line of the image sensors 12c to 12e is input at Step S109, the storage control circuitry 14b temporarily stores a video signal output from each line in the memory circuitry 14g.

Then, the control circuitry 14a increments the value of the variable N (Step S110). Then, in order to start imaging for the N-th frame, the control circuitry 14a outputs, to the image-sensor control circuitry 12f, the control signal for starting exposure for the N-th frame by using a rolling shutter method (Step S111). Here, each time a video signal output from each line of the image sensors 12e is input at Step S111, the storage control circuitry 14b temporarily stores a video signal output from each line in the memory circuitry 14g.

Then, at Step S112, the image processing circuitry 14c performs various types of image processing on the video signal (IR1) output from each line with respect to imaging for the first frame, the video signal (W2+IR2) output from each line with respect to imaging for the second frame, and the video signal (IR3) output from each line with respect to imaging for the third frame. Then, at Step 3112, the image synthesis circuitry 14d outputs the synthesis image W2+IR2+(IR1+IR3)/2) of the video signal (IR1), the video signal (W2+IR2), and the video signal (IRS) to the output circuitry 14e.

Then, the control circuitry 14a determines whether the command for terminating the control process has been received via the input device (Step S113). If the command for terminating the control process has not been received (Step S111; No), the control circuitry 14a increments the value of the variable N (Step S114) and returns to Step S102. Conversely, if the command for terminating the control process has been received (Step 113; Yes), the control circuitry 14a terminates the control process.

The imaging device 10 according to the first embodiment is explained above. With the imaging device 10 according to the first embodiment, as described above, it is possible to ensure the image quality sufficient for observation by users.

Furthermore, for example, an explanation is given of a case according to the technology disclosed in Patent Literature (WO 04/125724) where light (white light and IR excitation light) with two different wavelengths are alternately output, an imaging device outputs video signals at 120 [fps], and the exposure period is ¹/₆₀ [s]. In this case, white light images are output to a monitor at 30 [fps].

Conversely, according to the first embodiment, for example, if the image sensor 12c outputs video signals at 120 [fps] and the exposure period is ¹/₆₀ [s], color images based on white light are output to the display 101 at 60 [fps]. Therefore, with the imaging device according to the first embodiment, a reduction in the frame rate may be prevented. Therefore, it is possible to ensure the frame rate sufficient for observation by users.

Modification of the First Embodiment

Next, a modification of the first embodiment is explained. According to the first embodiment, the color image (W2+IR2) is an image based on video signals output from the image sensors 12c to 12e when white light and fluorescence are simultaneously received. Therefore, the color image (W2+IR2) is the synthesis image of a color image based on white light and a fluorescence image based on fluorescence. Thus, the color image (W2+IR2) includes a fluorescence image.

According to the first embodiment, it is assumed that the amount of fluorescence is vanishingly smaller than the amount of reflected light of white light; however, in a modification of the first embodiment, an explanation is given of a case where the amount of fluorescence is unignorably larger than the amount of reflected light of white light. In this case, as fluorescence images have a reddish color tone, the color image (W2+IR2) also has a reddish color tone.

Therefore, according to the modification of the first embodiment, the image processing circuitry 14c subtracts the synthesis image ((IR1+IR3)/2) of the fluorescence image (IR1) and the fluorescence image (IR3) from the color image (W2+IR2), thereby generating a color image based on only substantial white light. Specifically, the image processing circuitry 14c corrects the color image (W2+IR2) in such a manner that fluorescence components are reduced by using the fluorescence image (IR1) and the fluorescence image (IRS) generated before and after the color image (W2+IR2). Therefore, according to the modification of the first embodiment, it is possible to perform correction to reduce fluorescence components from the color image (W2+IR2). Here, fluorescence component is an example of component due to the first light.

Second Embodiment

Next, an imaging device according to a second embodiment is explained. In the second embodiment, the same configuration as that in the first embodiment is attached with the same reference numeral and explanation is sometimes omitted. The imaging device according to the second embodiment conducts the same operation as that of the imaging device 10 according to the first embodiment except that white light generated by the white LED 30b is controlled so that the brightness of an image becomes the target brightness. Furthermore, the configurations of the imaging device and the imaging system according to the second embodiment are the same as those in the first embodiment.

For example, the rolling-shutter type image sensors 12c to 12e have a shutter function with which, during imaging for a certain frame, all the electric charges stored in all the lines of pixels are discharged (reset) and after the electric charges are discharged, exposure is conducted again to restore electric charges. If this shutter function is performed, the light receiving period is sometimes not the same for the above-described line 44. In this case, images sometimes have uneven brightness.

Therefore, the imaging device according to the second embodiment controls white light generated by the white LED 30b such that the brightness of an image becomes the target brightness that is equal to or less than a threshold so that the shutter function is not performed.

Here, an explanation is given of an example of the method for calculating the brightness of an image. According to the second embodiment, the control circuitry 14a performs the following process on a per-frame basis. For example, the control circuitry 14a acquires, from the image processing circuitry 14c, the image data on the color image obtained as a result of various types of image processing conducted. Then, on a pixel by pixel basis, the control circuitry 14a selects the highest luminance from the R luminance, the G luminance, and the B luminance of each pixel included in the color image indicated by the image data. Here, for example, each pixel included in an image corresponds to each pixel in the image sensors 12c to 12e. Then, the control circuitry 14a calculates the sum of luminance selected for each pixel. Then, the control circuitry 14a divides the sum of calculated luminance by the number of pixels (pixel number) included in the image, thereby calculating the average value of luminance per pixel. Moreover, the control circuitry 14a handles the average value of calculated luminance as the brightness of the image.

Then, the control circuitry 14a compares the brightness of the image with the target brightness. Here, the target brightness is for example the value of luminance specified by a user. Furthermore, the target brightness is an example of predetermined brightness. If the target brightness is higher than the brightness of the image, the control circuitry 14a causes the timing-signal generation circuitry 14f to output a light-source control signal where the length of a high-level period is short in accordance with the difference between the brightness of the image and the target brightness so that the amount of white light emitted to the subject 100 becomes smaller. For example, as the difference between the brightness of the image and the target brightness is larger, the control circuitry 14a causes the timing-signal generation circuitry 14f to output a light-source control signal where the length of a high-level period is shorter. A specific example is given; the control circuitry 14a calculates the length of a high-level period in accordance with the difference between the brightness of the image and the target brightness and outputs, to the timing-signal generation circuitry 14f, the length of the high-level period obtained as a result of calculation. Thus, the timing-signal generation circuitry 14f outputs, to the drive circuitry 30a, the light-source control signal where the length of a high-level period is short.

Furthermore, if the target brightness is higher than the brightness of the image, the control circuitry 14a causes the timing-signal generation circuitry 14f to output a light-source control signal with a longer length of a high-level period within the range equal to or less than the read period in accordance with the difference between the brightness of the image and the target brightness.

That is, the control circuitry 14a and the timing-signal generation circuitry 14f control white light received by pixels by changing the length of a high-level period so that the brightness of the image becomes the target brightness. Specifically, the control circuitry 14a and the timing-signal generation circuitry 14f control the light receiving period so that the brightness of the image becomes the target brightness. The control circuitry 14a and the timing-signal generation circuitry 14f control the amount of white light emitted to the subject 100 by controlling the light receiving period. The control circuitry 14a and the generation circuitry 14f control the brightness of color images by controlling the light receiving period.

Third Embodiment

Next, the imaging device according to the third embodiment is explained. In explanation according to the third embodiment, the same configuration as that in each of the above-described embodiments and the above-described modification is attached with the same reference numeral and explanation is sometimes omitted.

The imaging device according to the third embodiment is used for a case where the amount of white light and excitation light (fluorescence) is sufficient or a case where white light and excitation light are prevented from being mixed.

Figure 6:
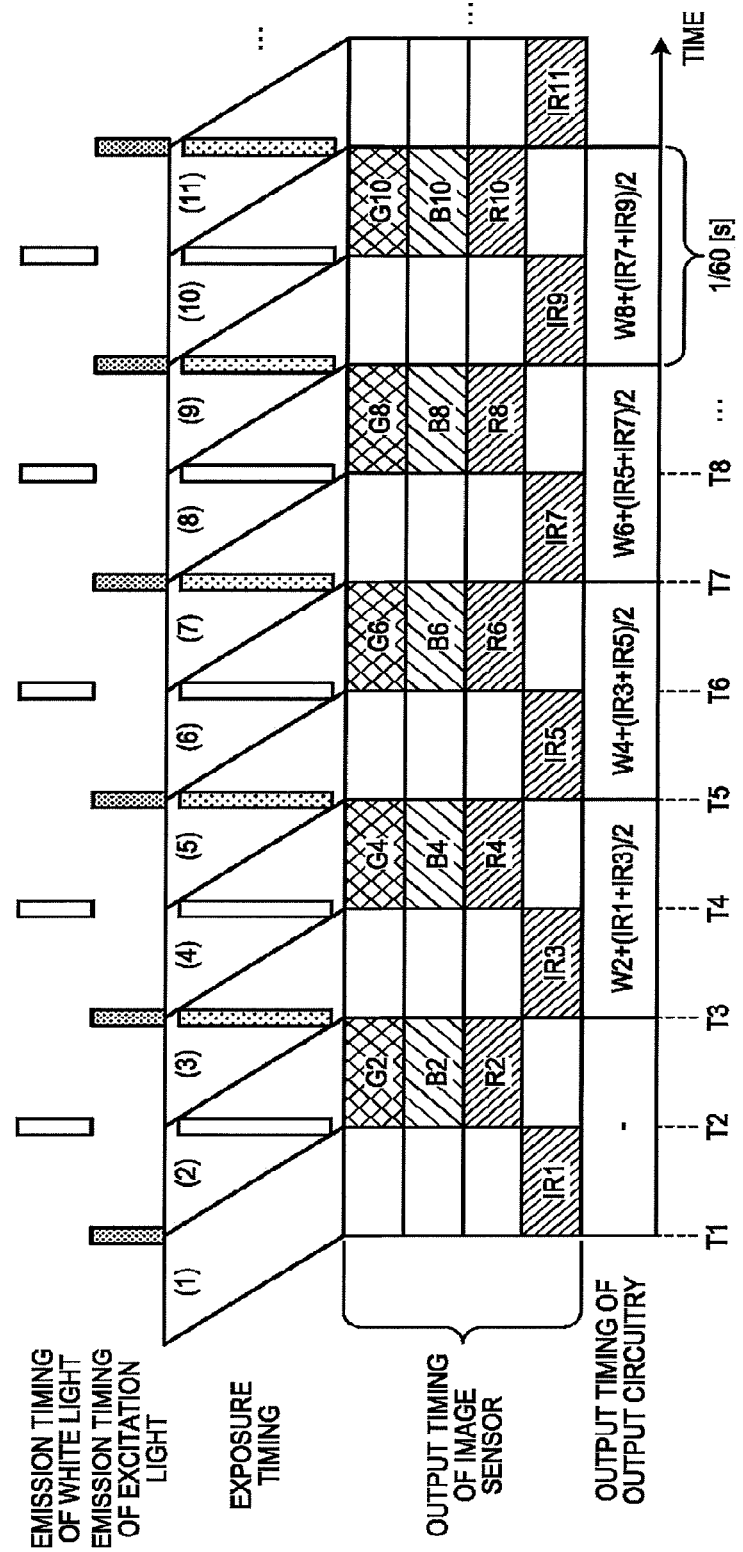
FIG. 6 is a diagram that illustrates an example operation of the imaging device according to a third embodiment.

FIG. 6 is a diagram that illustrates an example of operation of the imaging device according to the third embodiment. FIG. 6 illustrates an example of the relation among the emission timing of white light and excitation light output from the light source device 30 according to the third embodiment; the exposure timing on each line of pixels included in the image sensors 12c to 12e of the imaging device 10; the output timing of video signals output from the image sensors 12c to 12e; and the output timing of video signals output from the output circuitry 14e. In FIG. 6, the horizontal axis indicates a time.

An explanation is given of the different point between the operation of the imaging device according to the third embodiment illustrated in FIG. 6 and the operation of the imaging device 10 according to the first embodiment illustrated in FIG. 3. In the first embodiment, an explanation is given of a case where the control circuitry 14a causes excitation light to be continuously output. However, according to the third embodiment, the control circuitry 14a switches the type of light received by pixels on a frame-to-frame basis. Specifically, the control circuitry 14a alternately switches the light output from the light source device 30 to white light or excitation light on a per-frame basis. Thus, the control circuitry 14a alternately switches the light received by pixels to white light or excitation light on a per-frame basis.

According to tree third embodiment, the control circuitry 14a causes the light source device 30 to alternately output excitation light and white light, which are different types, in synchronization with the blanking period or the period centered on the blanking period. The image processing circuitry 14c generates a fluorescence image on the basis of video signals generated by pixels due to reception of fluorescence based on excitation light and generates a color image on the basis of video signals generated by pixels due to reception of white light. The image synthesis circuitry 14d generates a synthesis image by using the fluorescence image and the color image. Here, video signals generated by pixels in the image sensor 12e due to reception of fluorescence based on excitation light are an example of the first electric signal. Video signals generated by pixels in the image sensors 12c to 12e due to reception of white light are an example of the second electric signal.

As is the case with the first embodiment, the imaging device according to the third embodiment may ensure the image quality sufficient observation.

Furthermore, an explanation is given of a case where according to the technology disclosed in Patent Literature (WO 2014/125724), for example, two types of light (white light and IR excitation light) with different wavelengths are alternately output, an imaging device outputs video signals at 120 [fps], and the exposure period is 1/60 [s]. In this case, white light images and fluorescence observation images are output to a monitor at 30 [fps].

Conversely, according to the third embodiment, for example, if two types of light (white light and excitation light) with different wavelengths are alternately output, the image sensors 12c to 12e output video signals at 120 [fps], and the exposure period is 1/60 [s], synthesis images of color images based on white light and fluorescence images based on fluorescence are output to the display 101 at 60 [fps]. Therefore, with the imaging device according to the third embodiment, a reduction in the frame rate may be prevented.

Fourth Embodiment

Next, an imaging device according to the fourth embodiment is explained. In explanation according to the fourth embodiment, the same configuration as that in each of the above-described embodiments and the above-described modification is attached with the same reference numeral and explanation is sometimes omitted.

In the first embodiment, for example, an explanation is given of a case where the pixels of the image sensors 12 to 12e receive light during only the period where its center is a blanking period and 1/1200 [s] is added to the blanking period. In this case, masked areas are approximately 10% of the entire screen area.

Figure 7:
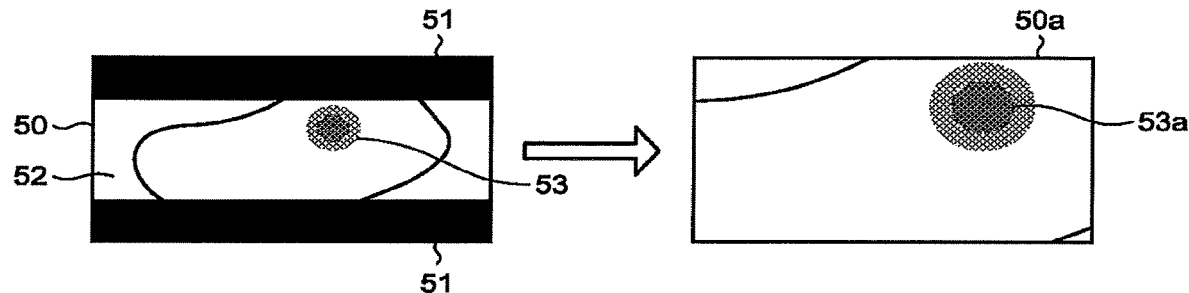
FIG. 7 is a diagram that illustrates an example of the image according to a fourth embodiment.

FIG. 7 is a diagram that illustrates an example of the image according to the fourth embodiment. To ensure the amount of light, however, approximately 50% of the entire screen area may be masked areas, as illustrated in the example of FIG. 7, for instance, by increasing the light receiving period of the pixels in the image sensors 12c to 12e. In this case, the image processing circuitry 14c may generate an image (enlarged image) 50a where the effective image area 52 has been enlarged. As it has been enlarged as illustrated in the example of FIG. 7, users can observe a marker 53a more easily.

Fifth Embodiment

Next, the imaging device according to the fifth embodiment is explained. In explanation according to the fifth embodiment, the same configuration as that in each of the above-described embodiments and the above-described modification is attached with the same reference numeral and explanation is sometimes omitted.

The control circuitry 14a in the imaging device according the fifth embodiment switches a mode (first mode) for performing a control process according to one embodiment among the first embodiment to the fourth embodiment and a mode (second mode) for conducting capturing for color images based on white light or fluorescence images based on excitation light by driving only the white LED 30b or the IR laser 30d in accordance with user's instructions.

For example, in the second mode, the exposure period is 1/60 that is twice as long as the exposure period 1/120 [s] according to the first to fourth embodiments. Furthermore, in the second mode, the control circuitry 14a causes the pixels in the image sensors 12c to 12e to receive fluorescence or white light so that fluorescence images or color images are output to the display 101 at a predetermined frame rate 1/60.

Figure 8:
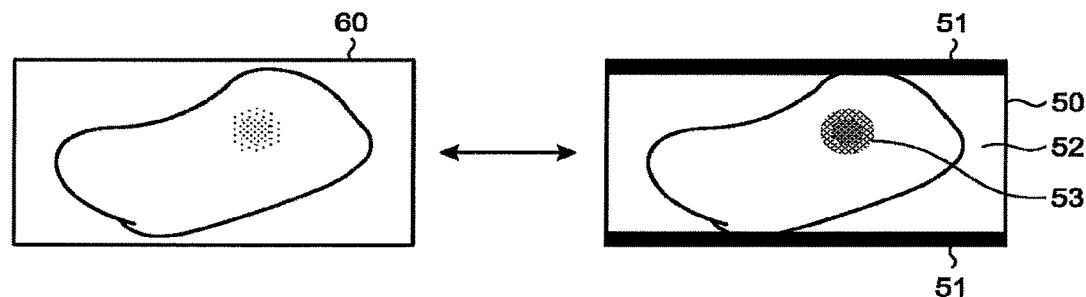
FIG. 8 is a diagram that illustrates an example of mode changes conducted by the imaging device according to a fifth embodiment.

FIG. 8 is a diagram that illustrates an example of mode changes conducted by the imaging device according to the fifth embodiment. As illustrated in the example of FIG. 8, for example, if there is an area that needs to be examined in the middle of observation on a color image 60 while in the second mode, a user such as a doctor inputs a command to make a switch to the first mode via an input device (not illustrated). In accordance with the input user's command, the control circuitry 14a makes a switch to the first mode and causes the display 101 to present the synthesis image where the marker 53 is superimposed on the color image 50.

According to the fifth embodiment, even if a mode is changed, the frame rate for output from the imaging device to the display 101 is not changed. Therefore, with the imaging device according to the fifth embodiment, it is possible to reduce user's uncomfortable feelings when a mode is switched.

Sixth Embodiment

Next, an imaging device according to a sixth embodiment is explained. In the first embodiment to the fourth embodiment and the modification of the first embodiment described above, an explanation is given of a case where the control circuitry 14a causes the pixels to receive light during only the blanking period, the period within the blanking period, or the period centered on the blanking period as a period based on the blanking period. However, the control circuitry 14a may cause the pixels to receive light during only part of the period centered on the blanking period as a period based on the blanking period. Thus, this embodiment is explained as the sixth embodiment.

Figure 9:
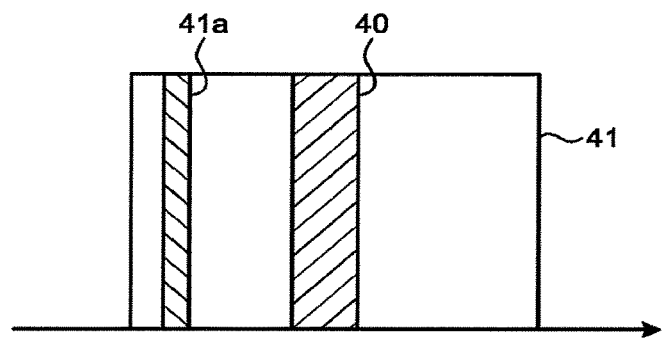
FIG. 9 is a diagram that illustrates an example of operation of an imaging device according to a sixth embodiment.

FIG. 9 is a diagram that illustrates an example of operation of an imaging device according to the sixth embodiment. In FIG. 9, the horizontal axis indicates time. For example, an explanation is first given of a case where, as is the case with the first embodiment, the control circuitry 14a causes the light source device 30 to continuously output excitation light and causes the light source device 30 to output white light once in two frames in synchronization with a period based on the blanking period 40.

In this case, as illustrated in FIG. 9, the control circuitry 14a causes the light source device 30 to output white light once in two frames during only a period 41a that is part of the period 41 centered on the blanking period 40. Thus, the pixels receive light during only the period 41a that is part of the period 41. Here, the period 41a is a period arranged before the blanking period 40 in chronological order.

Next, an explanation is given of a case where, as is the case with the third embodiment, the control circuitry 14a causes the light source device 30 to alternately output excitation light and white light, which are different types, in synchronization with a period based on the blanking period 40.

In this case, too, as illustrated in FIG. 9, the control circuitry 14a causes the light source device 30 to alternately output excitation light and white light during only the period 41a. This also allows the pixels to receive light during only the period 41a that is part of the period 41.

According to the sixth embodiment, although the size of a masked area at one end side of the synthesis image presented on the display 101 is different from the size of a masked area at the other end side, it is possible to ensure the frame rate and the image quality sufficient for observation by users such as doctors who observe images, as is the case with other embodiments.

Each embodiment has been described above. Here, in each embodiment, the case where the imaging device 10 causes the image sensors 12c to 12e to receive reflected light of white light and performs various operations has been described. However, for example, the imaging device 10 may cause the image sensor 12e to receive fluorescence (fluorescence based on white light) which is output from ICG after ICG is excited by white light and perform the similar operation.

With the above-described imaging device according to at least one of the embodiments or the modification, the frame rate sufficient for user's observation may be ensured.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An imaging device comprising:
   a rolling-shutter type image sensor that
      includes a plurality of pixels that are arranged in a matrix and generate an electric signal due to light received, and
      on a frame-to-frame basis, repeatedly performs a process to sequentially start to conduct exposure on at least every line, starting from a first line of the pixels to a last line, and output the electric signal sequentially from a line for which exposure has been completed; and
   processing circuitry that
      causes the pixels to receive light during only a period based on a blanking period that corresponds to a period from when output of the electric signal from the last line is finished until output of the electric signal from the first line is started,
      generates an image in accordance with the electric signal, and
      sets, in the image, an effective image area except for at least edges of the image corresponding to the first line and the last line.

2. The imaging device according to claim 1, wherein the period based on the blanking period is the blanking period, a period within the blanking period, a period centered on the blanking period, or a partial period of the period centered on the blanking period.

3. The imaging device according to claim 1, wherein the processing circuitry causes the pixels to receive light during a period that is equal to or less than a period from when output of the electric signal from the first line of one frame is started until output of the electric signal from the last line of the one frame is finished.

4. The imaging device according to claim 1, wherein the processing circuitry generates the image where an area other than the effective image area is replaced with a different image.

5. The imaging device according to claim 1, wherein the processing circuitry generates the image where the effective image area has been enlarged.

6. The imaging device according to claim 1, wherein the processing circuitry controls brightness of the image by controlling a light receiving period of the pixel.

7. The imaging device according to claim 1 comprising:
   a plurality of image sensors each of which is the image sensor, wherein
   each of the image sensors outputs an electric signal when receiving corresponding type of light.

8. An imaging device comprising:
   a rolling-shutter type image sensor that
      includes a plurality of pixels that are arranged in a matrix and generate an electric signal due to light received, and
      on a frame-to-frame basis, repeatedly performs a process to sequentially start to conduct exposure on at least every line, starting from a first line of the pixels to a last line, and output the electric signal sequentially from a line for which exposure has been completed; and
   processing circuitry that
      causes the pixels to receive light during only a period based on a blanking period that corresponds to a period from when output of the electric signal from the last line is finished until output of the electric signal from the first line is started, and
      generates an image in accordance with the electric signal,
   wherein the processing circuitry further
      causes a light source device to continuously output first light and causes the light source device to output second light, which is a different type from the first light, once in two frames in synchronization with the period based on the blanking period,
      generates a first image in accordance with a first electric signal generated by the pixels due to reception of reflected light of the first light or fluorescence generated due to the first light, generates a second image in accordance with a second electric signal generated by the pixels due to simultaneous reception of reflected light of the first light or the fluorescence and reflected light of the second light or fluorescence generated due to the second light, and
      generates the image by using the first image and the second image.

9. The imaging device according to claim 8, wherein the processing circuitry generates the image by using the second image and the first images generated before and after the second image.

10. The imaging device according to claim 9, further comprising an optical device that is arranged by being opposed to an imaging area of the pixels and that causes the pixels to receive light other than excitation light output as the first light from the light source device.

11. The imaging device according to claim 8, wherein the processing circuitry corrects the second image such that a component due to the first light is reduced by using the first images generated before and after the second image.

12. The imaging device according to claim 8, further comprising an optical device that is arranged by being opposed to an imaging area of the pixels and that causes the pixels to receive light other than excitation light output as the first light from the light source device.

13. The imaging device according to claim 8, wherein in accordance with a command, the processing circuitry makes a switch between a first mode for causing the pixels to receive light during only the period based on the blanking period in a predetermined exposure period of the pixels and outputting the image at a predetermined frame rate and a second mode for causing the pixels to receive one light among the reflected light of the first light, the fluorescence generated due to the first light, the reflected light of the second light and the fluorescence generated due to the second light during an exposure period that is twice as long as the predetermined exposure period and outputting an image that is based on the one light at the predetermined frame rate.

14. The imaging device according to claim 8, wherein the processing circuitry generates the image that is a synthesis of the first image and the second image.

15. An imaging device comprising:
a rolling-shutter type image sensor that
   includes a plurality of pixels that are arranged in a matrix and generate an electric signal due to light received, and
   on a frame-to-frame basis, repeatedly performs a process to sequentially start to conduct exposure on at least every line, starting from a first line of the pixels to a last line, and output the electric signal sequentially from a line for which exposure has been completed; and
processing circuitry that
   causes the pixels to receive light during only a period based on a blanking period that corresponds to a period from when output of the electric signal from the last line is finished until output of the electric signal from the first line is started, and
   generates an image in accordance with the electric signal,
wherein the processing circuitry further
   causes a light source device to alternately output first light and second light, which are different types, in synchronization with the period based on the blanking period, and
   generates a first image in accordance with a first electric signal generated by the pixels due to reception of reflected light of the first light or fluorescence generated due to the first light, generates a second image in accordance with a second electric signal generated by the pixels due to reception of reflected light of the second light or fluorescence generated due to the second light, and
   generates the image by using the first image and the second image.

16. The imaging device according to claim 15, wherein the processing circuitry generates the image by using the second image and the first images generated before and after the second image.

17. The imaging device according to claim 16, further comprising an optical device that is arranged by being opposed to an imaging area of the pixels and that causes the pixels to receive light other than excitation light output as the first light from the light source device.

18. The imaging device according to claim 15, further comprising an optical device that is arranged by being opposed to an imaging area of the pixels and that causes the pixels to receive light other than excitation light output as the first light from the light source device.

19. The imaging device according to claim 15, wherein in accordance with a command, the processing circuitry makes a switch between a first mode for causing the pixels to receive light during only the period based on the blanking period in a predetermined exposure period of the pixels and outputting the image at a predetermined frame rate and a second mode for causing the pixels to receive one light among the reflected light of the first light, the fluorescence generated due to the first light, the reflected light of the second light and the fluorescence generated due to the second light during an exposure period that is twice as long as the predetermined exposure period and outputting an image that is based on the one light at the predetermined frame rate.

20. A control method implemented by an imaging device including a rolling-shutter type image sensor that includes a plurality of pixels that are arranged in a matrix and generate an electric signal due to light received and, on a frame-to-frame basis, repeatedly performs a process to sequentially start to conduct exposure on at least every line, starting from a first line of the pixels to a last line, and output the electric signal sequentially from a line for which exposure has been completed, the control method comprising:
   causing the pixels to receive light during only a period based on a blanking period that corresponds to a period from when output of the electric signal from the last line is finished until output of the electric signal from the first line is started,
   generating an image in accordance with the electric signal, and
   setting, in the image, an effective image area except for at least edges of the image corresponding to the first line and the last line.

* * * * *